United States Patent [19]

Gayer et al.

[11] Patent Number: 4,886,833
[45] Date of Patent: Dec. 12, 1989

[54] 2-CYANO-2-ALKOXIMINO-ACETAMIDES

[75] Inventors: Herbert Gayer, Monheim; Klaus Jelich; Winfried Lunkenheimer, both of Wuppertal; Wilhelm Brandes, Leichlingen; Gerd Hänssler, Leverkusen, all of Fed. Rep. of Germany

[73] Assignee: Bayer Aktiengesellschaft, Leverkusen, Fed. Rep. of Germany

[21] Appl. No.: 88,922

[22] Filed: Aug. 24, 1987

[30] Foreign Application Priority Data

Sep. 10, 1986 [DE] Fed. Rep. of Germany ....... 3630732

[51] Int. Cl.$^4$ ................... C07C 131/00; A01N 37/44
[52] U.S. Cl. .................................. 514/521; 514/528; 548/195; 588/391; 588/392; 588/442; 588/445
[58] Field of Search ............... 558/445, 442, 391, 392; 514/521, 528

[56] References Cited

U.S. PATENT DOCUMENTS 3,954,992  5/1976  Davidson ........................... 424/287
3,957,847  5/1976  Davidson ......................... 260/465.4

FOREIGN PATENT DOCUMENTS 0075821   4/1983  European Pat. Off. .
0088325   9/1983  European Pat. Off. .
0201999  11/1986  European Pat. Off. .
0206004  12/1986  European Pat. Off. .
0250744   1/1988  European Pat. Off. .
2312956   9/1973  Fed. Rep. of Germany .
2173791  10/1986  United Kingdom ............... 558/445

OTHER PUBLICATIONS

Chemical Abstracts, vol. 70, No. 12; Mar. 24, 1969; p. 321.

*Primary Examiner*—Robert Gerstl
*Attorney, Agent, or Firm*—Sprung Horn Kramer & Woods

[57] ABSTRACT

Novel fungicides of the formula

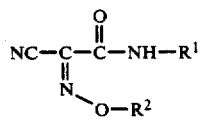

in which
R$^1$ represents optionally substituted hydroxyalkyl, optionally substituted hydroxyalkoxyalkyl, optionally substituted heteroarylalkyl or optionally substituted heteroaryl, and
R$^2$ represents optionally substituted alkyl, optionally substituted alkenyl, or alkinyl.

Intermediate therefor, wherein R$^2$ is hydrogen or an alkali metal cation, are also new.

9 Claims, No Drawings

2-CYANO-2-ALKOXIMINO-ACETAMIDES

The invention relates to new 2-cyano-2-alkoximinoacetamides, a process for the preparation of these, and the use of these as pesticides.

It is already known that organic acid derivatives, such as, for example, zinc ethylene-1,2-bis-dithiocarbamate, have fungicidal properties (cf., for example, K. H. Büchel "Pflanzenschutz and Schädlingbekämpfung" [Plant Protection and Combating Pests] p. 137, G. Thieme Verlag, Stuttgart 1977).

However, the activity of this compound is not completely satisfactory in all areas of application, particularly when low amounts are applied and at low concentrations.

In addition, 2-cyano-2-alkoximino-N-alkyl-acetamides and 2-cyano-2-alkoximino-N-alkylaminocarbonyl-acetamides have been disclosed as fungicides (cf. DE-OS (German Published Specification) 2,312,956).

New 2-cyano-2-alkoximino-acetamides of the general formula (I),

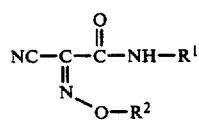

in which
R¹ represents optionally substituted hydroxyalkyl, optionally substituted hydroxyalkoxyalkyl, optionally substituted heteroarylalkyl or optionally substituted heteroaryl, and
R² represents optionally substituted alkyl, optionally substituted alkenyl, or alkinyl,
have been found.

The compounds of the formula (I) can exist as geometrical isomers or as isomer mixtures of various composition. The pure isomers and the isomer mixtures are claimed according to the invention.

It has furthermore been found that the new 2-cyano-2-alkoximino-acetamides of the general formula (I),

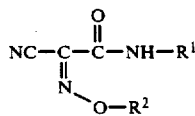

in which
R¹ represents optionally substituted hydroxyalkyl, optionally substituted hydroxyalkoxyalkyl, optionally substituted heteroarylalkyl or optionally substituted heteroaryl, and
R² represents optionally substituted alkyl, optionally substituted alkenyl, or alkinyl,
are obtained when 2-cyano-2-oximino-acetamides of the formula (II)

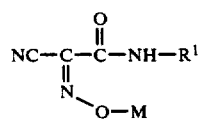

in which
M represents hydrogen or an alkali metal cation, and R¹ has the abovementioned meaning,
are reacted with alkylating agents of the formula (III), $$R^2-A \qquad (III)$$

in which
A represents a suitable leaving group, and
R² has the abovementioned meaning,
if appropriate in the presence of a diluent and if appropriate in the presence of an acid-binding agent.

Finally, it has been found that the new 2-cyano-2-alkoximino-acetamides of the general formula (I) have an action against pests.

Surprisingly, the 2-cyano-2-alkoximino-acetamides, according to the invention, of the general formula (I) have, for example, a better fungicidal action than the compound zinc ethylene-1,2-bis-dithiocarbamate which is known from the state of the art and which is a similar compound regarding its action.

Formula (I) provides a general definition of the 2-cyano-2-alkoximino-acetamides. Preferred compounds of the formula (I) are those in which:
R¹ represents in each case straight-chain or branched, optionally phenyl-substituted hydroxyalkyl or hydroxyalkoxyalkyl in each case having 1 to 6 carbon atoms in the individual alkyl parts, or, in addition, represents heteroarylalkyl or heteroaryl, in each case having 2 to 10 carbon atoms and 1 to 3 heteroatoms, in particular nitrogen, oxygen or sulphur, in the heteroaryl part and, in the case of heteroarylalkyl, having 1 to 6 carbon atoms in the straight-chain or branched alkyl part, which is optionally monosubstituted or polysubstituted and/or benzene-fused, the substituents being identical or different and suitable substituents of the heteroaryl parts and/or of the benzene-fused rings in each case being: hydroxyl, halogen, cyano, in each case straight-chain or branched alkyl, alkenyl, alkoxy or alkylthio in each case having up to 4 carbon atoms, aralkyl having 6 to 10 carbon atoms in the aryl part and 1 to 3 carbon atoms in the straight-chain or branched alkyl part, aryl having 6 to 10 carbon atoms, alkylcarbonyl, alkoxycarbonyl, alkylaminocarbonyl and dialkylaminocarbonyl in each case having 1 to 4 carbon atoms in the individual straight-chain or branched alkyl parts, and
R² represents straight-chain or branched alkyl, having 1 to 18 carbon atoms, which is optionally monosubstituted or polysubstituted, the substituents being identical or different and substituents which may be mentioned being: cyano, in each case straight-chain or branched alkanoyl, alkoxycarbonyl or alkylcarbonyloxy in each case having 1 to 6 carbon atoms in the individual alkyl parts, and phenyl or heteroaryl, having 2 to 9 carbon atoms and 1 to 3 heteroatoms, in particular nitrogen, oxygen and sulphur, which is in each case optionally monosubstituted or polysubstituted by lower alkyl and/or halogen; and in addition represents in each case straight-chain or branched alkenyl or halogenoalkenyl in each case having 3 to 8 carbon atoms and, in the case of halogenoalkenyl, having 1 to 5 halogen atoms, or straight-chain or branched alkinyl having 3 to 8 carbon atoms. Particularly preferred compounds of the formula
(I) are those in which
R¹ represents in each case straight-chain or branched, optionally phenyl-substituted hydroxyalkyl or hydroxyalkoxyalkyl in each case having 1 to 4 carbon atoms in individual alkyl parts, in addition represents heteroarylalkyl or heteroaryl, in each case having 2 to 10 carbon atoms and 1 to 3 nitrogen and/or oxygen and/or sulphur atoms in the heteroaryl part and 1 to 4 carbon atoms in the straight-chain or branched alkyl part, which is in each case optionally monosubstituted, disubstituted or trisubstituted and/or benzene-fused, the substituents being identical or different and suitable substituents in the heteroaryl part and/or in the benzene-fused ring being the following: hydroxyl, fluorine, chlorine, bromine, cyano, methyl, ethyl, n- or i- propyl, n-, i-, s- or t-butyl, allyl, butenyl, methoxy, ethoxy, methylthio, benzyl, phenyl, acetyl, propionyl, methoxycarbonyl, ethoxycarbonyl, methylaminocarbonyl or dimethylaminocarbonyl, and $R^2$ represents straight-chain or branched alkyl, having 1 to 12 carbon atoms, which is optionally monosubstituted, disubstituted or trisubstituted, the substituents being identical or different and substituents which may be mentioned being: cyano, acetyl, propionyl, methoxycarbonyl, ethoxycarbonyl, methylcarbonyloxy, ethylcarbonyloxy, or phenyl or heteroaryl which is in each case optionally monosubstituted, disubstituted or trisubstituted by fluorine, chlorine, bromine, methyl and/or ethyl, the substituents being identical or different and the following being suitable as heteroaryl: pyridyl, pyrimidyl, triazinyl, quinolyl, isoquinolyl, oxazolyl, isoxazolyl, oxadiazolyl, benzoxazolyl, thiazolyl, isothiazolyl, thiadiazolyl, benzthiazolyl, imidazolyl, benzimidazolyl, pyrrolyl, furanyl, thienyl, pyrazolyl or triazolyl; in addition represents in each case straight-chain or branched alkenyl or halogenoalkenyl having 3 to 6 carbon atoms and, if appropriate, 1 to 3 halogen atoms, or straight-chain or branched alkinyl having 3 to 6 carbon atoms.

Very particularly preferred compounds of the formula (I) are those in which $R^1$ represents in each case straight-chain or branched, optionally phenyl-substituted hydroxyalkyl or hydroxyalkoxyalkyl in each case having 1 to 4 carbon atoms in the individual alkyl parts, or, additionally, represents heteroaryl or heteroarylalkyl, having 1 to 4 carbon atoms in the straight-chain or branched alkyl part, which is in each case optionally monosubstituted, disubstituted or trisubstituted, the substituents being identical or different and it being possible for the heteroaryl radical to be the following in each case: pyridyl, pyrimidyl, triazinyl, quinolyl, isoquinolyl, oxazolyl, isoxazolyl, oxadiazolyl, benzoxazolyl, thiazolyl, isothiazolyl, thiadiazolyl, benzthiazolyl, imidazolyl, benzimidazolyl, pyrrolyl, furanyl, thienyl, pyrazolyl or triazolyl and the following being suitable in each case as substituents in the heteroaryl part or in the benzene-fused ring: hydroxyl, fluorine, chlorine, bromine, cyano, methyl, ethyl, n- or i-propyl, n-, i-, s- or t-butyl, allyl, butenyl, methoxy, ethoxy, methylthio, benzyl, phenyl, acetyl, propionyl, methoxycarbonyl, ethoxycarbonyl, methylaminocarbonyl or dimethylaminocarbonyl, and $R^2$ represents straight-chain or branched alkyl, having 1 to 12 carbon atoms, which is optionally monosubstituted, disubstituted or trisubstituted, the substituents being identical or different and substituents which may be mentioned being: cyano, acetyl, propionyl, methoxycarbonyl, ethoxycarbonyl, methylcarbonyloxy, ethylcarbonyloxy, or phenyl which is optionally monosubstituted, disubstituted or trisubstituted by fluorine, chlorine, bromine, methyl and/or ethyl, the substituents being identical or different; or in addition represents in each case straight-chain or branched alkenyl or halogenoalkenyl having 3 to 6 carbon atoms and, if appropriate, 1 to 3 halogen atoms, or straight-chain or branched alkinyl having 3 to 6 carbon atoms.

The compounds mentioned in the preparation examples may be mentioned individually.

If, for example, the sodium salt of 3-(2-cyano-2-oximino-acetamido)-5-methyl-isoxazole and dimethyl sulphate are used as starting materials, the course of the reaction of the process according to the invention can be represented by the following equation:

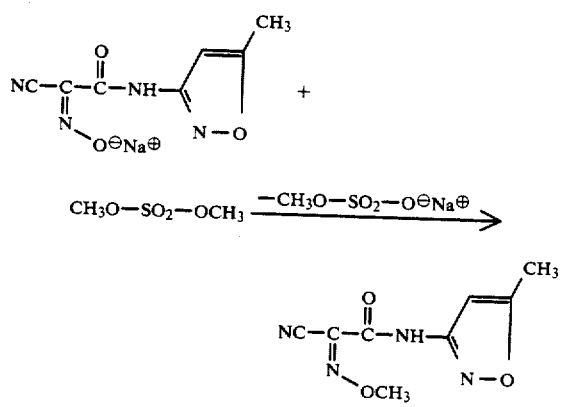

Formula (II) provides a general definition of the 2-cyano-2-oximino-acetamides which are required as starting materials for carrying out the process according to the invention. Preferred compounds of the formula (II) are those in which $R^1$ represents those radicals which have already been mentioned for these substituents in connection with the description of the compounds, according to the invention, of the formula (I) and in which M represents hydrogen or a sodium cation.

The 2-cyano-2-oximino-acetamides of the formula (II) were hitherto not known.

They are obtained analogously to known processes (cf., for example, Ber. dtsch. chem. Ges. 42, 738 [1909] or J. Pharm. Sci. 67, 860 [1978]), when cyanoacetic acid or activated cyanoacetic acid derivatives of the formula (IV),

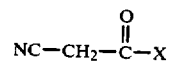

in which
X represents an activating leaving group, such as, for example, halogen, methoxy, ethoxy, acetoxy or methanesulphonyloxy, are reacted with amines of the formula (V),

in which
$R^1$ has the abovementioned meaning, at temperatures between −40° C. and +50° C., if appropriate in the presence of a diluent, such as, for example, pyridine, dimethylformamide or tetrahydrofuran, and if appropriate in the presence of an acid-binding agent such as, for example, triethylamine. In this reaction, the activated cyanoacetic acid derivatives of the formula (IV), such as, for example, mixed anhydrides with acetic acid or methanesulphonic acid, can alternatively first be prepared in the reaction mixture by employing the cyanoacetic acid as such and adding, for example, acetic anhydride or methanesulphonyl chloride in the presence of a base, such as, for example, pyridine. The 2-cyanoacetamides of the formula (VI),

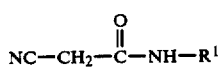
(VI)

in which
R$^1$ has the abovementioned meaning,
thus obtainable are reacted, in a second stage, with a nitrite compound of the formula (VII),

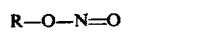
(VII)

in which
R represents an alkali metal cation, in particular a sodium cation, or an alkyl radical, in particular an ethyl, t-butyl or isoamyl radical,
at temperatures between −20° C. and +120° C., if appropriate in the presence of a diluent, such as, for example, water, methanol, ethanol or tetrahydrofuran, if appropriate in the presence of a catalyst acid, such as, for example, hydrochloric acid or acetic acid, or alternatively in the presence of a base, such as, for example, sodium amide, sodium methylate or sodium ethylate.

Cyanoacetic acid and the activated derivatives thereof of the formula (IV), the amines of the formula (V) and the nitrite compounds of the formula (VII) are generally known compounds of organic chemistry.

Formula (III) provides a general definition of the alkylating agents which are furthermore required as starting materials for carrying out the process according to the invention. In this formula (III), R$^2$ preferably represents those radicals which have already been mentioned in connection with the description of the substances, according to the invention, of the formula (I) as being preferred for this substituent.

A preferably represents halogen, in particular chlorine, bromine or iodine, or in each case optionally substituted alkylsulphonyloxy, alkoxysulphonyloxy or arylsulphonyloxy, such as, for example, methanesulphonyloxy, methoxysulphonyloxy or p-toluenesulphonyloxy.

The alkylating agents of the formula (III) are generally known compounds of organic chemistry.

Suitable diluents for carrying out the process according to the invention are inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, dichloromethane, chloroform and carbon tetrachloride; ethers, such as diethyl ether, dioxane, tetrahydrofuran, ethyleneglycol dimethyl ether or ethylene glycol diethyl ether: ketones, such as acetone or butanone; nitriles, such as acetonitrile or propionitrile; amides, such as dimethylformamide, dimethylacetamide, N-methylformanilide, N-methylpyrrolidone or hexamethylphosphoric triamide, esters, such as ethyl acetate; sulphoxides, such as dimethyl sulphoxide, or alcohols, such as methanol, ethanol or isopropanol.

The process according to the invention can, if appropriate, alternatively be carried out in a two-phase system, such as, for example, water/toluene or water/dichloromethane, if appropriate in the presence of a phasetransfer catalyst. Examples of such catalysts which may be mentioned are: tetrabutylammonium iodide, tetrabutylammonium bromide, tributyl-methylphosphonium bromide, trimethyl-$C_{13}$/$C_{15}$-alkylammonium chloride, dibenzyldimethyl-ammonium methylsulphate, dimethyl-$C_{12}$/$C_{14}$-alkylbenzylammonium chloride, tetrabutylammonium hydroxide, 15-crown-5, 18-crown-6, triethylbenzylammonium chloride and trimethylbenzylammonium chloride.

Suitable acid-binding agents for carrying out the process according to the invention are all inorganic or organic bases which can conventionally be used. Preferably used are alkali metal hydrides, alkali metal hydroxides, alkali metal alcoholates, alkali metal amides, alkali metal carbonates or alkali metal hydrogen carbonates, such as, for example, sodium hydride, sodium amide, sodium hydroxide, sodium ethylate, sodium carbonate or sodium hydrogen carbonate, or alternatively tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU).

The reaction temperatures can be varied within a relatively wide range when carrying out the process according to the invention. In general, the process is carried out at temperatures between −20° C. and 100° C., preferably at temperatures between 0° C. and 60° C.

To carry out the process according to the invention, 1.0 to 5.0 mols, preferably 1.0 to 3.0 mols, of alkylating agent of the formula (III) and 1.0 to 5.0 mols, preferably 1.0 to 3.0 mols, of acid-binding agent and, if appropriate, 0.001 to 1.0 mol of phase-transfer catalyst are generally employed per mol of 2-cyano-2-oximinoacetamide of the formula (II).

In a preferred form of carrying out the process, it is also possible to prepare, as described above, the 2-cyano-2-oximino-acetamides of the formula (II) used as starting materials and to further react them with the alkylating agents of the formula (III) directly from the reaction mixture in a "one-pot process" (cf. preparation examples). The reaction is carried out and the reaction products of the formula (I) are worked up and isolated by conventional methods.

The active compounds according to the invention have a strong action against pests and can be employed in practice for combating undesired pests. The active compounds are suitable, for example, for use as plant-protection agents.

Thus, for example, fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum*; Phytophthora species, such as, for example, *Phytophthora infestans*; Pseudoperonospora species, such as, for example, *Pseudoperonospora humuli* or *Pseudopero-*

*nospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

In this treatment, the active compounds according to the invention can be used particularly successfully for combating Oomycetes, such as, for example against the pathogen of tomato brown rot (*Phytophthora infestans*) or against the pathogen of downy mildew of the pea (*Peronospora pisi*), or for combating rice diseases, such as, for example, against the pathogen of rice spot (*Pyricularia oryzae*). It should be particularly emphasized that the active compounds according to the invention not only show a protective action but also have a curative action, i.e. when used after contamination of the plants by the fungal spores.

In addition, the systemic action of the substances is pointed out. Thus, plants can be successfully protected against fungal infestation, for example by dressing the seed with the active compounds.

The active compounds can be converted to the customary formulations, such as solutions, emulsions, wettable powders, suspensions, powders, dusting agents, foams, pastes, soluble powders, granules, aerosols, suspension/emulsion concentrates, seed powder, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorilonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, and also natural phospholipids, such as cephalins and lecithins, can be used in the formulations. Further additives can be mineral and vegtable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

Preparation examples

EXAMPLE 1:

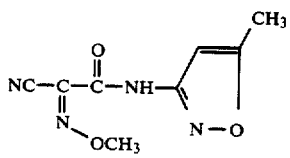

2 g (0.03 mol) of sodium ethylate in 15 ml of ethanol are added with stirring to 5 g (0.03 mol) of 3-cyanoacetamido-5-methyl-isoxazole and 3.5 g (0.03 mol) of isoamyl nitrite in 30 ml of ethanol at 25° C., and the mixture is warmed at 50° C. for one minute. After cooling to room temperature, 3.8 g (0.03 mol) of dimethyl sulphate are added, and the reaction mixture is allowed to stand for one hour. The solvent is then removed by distillation in vacuo, and the residue is chromatographed using ethyl acetate as eluent.

3.3 g (53% of theory) of 3-(2-cyano-2-methoximinoacetamido)-5-methyl-isoxazole of melting point 197°–199° C. are obtained.

Preparation of the starting compound

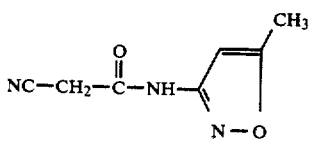

10.2 g (0.1 mol) of acetic anhydride in 50 ml of pyridine are added to 8.5 g (0.1 mol) of cyanoacetic acid and 9.8 g (0.1 mol) of 3-amino-5-methyl-isoxazole in 50 ml of pyridine at room temperature. Immediately thereafter, the pyridine is removed in vacuo, and the residue is taken up in toluene, concentrated, taken up a second time in toluene, again concentrated, treated with 100 ml of water, filtered off under suction, washed with water and dried.

15.3 g (93% of theory) of 3-cyanoacetamido-5-methyl-isoxazole of melting point 225°–227° C. (decomp.) are obtained.

EXAMPLE 2

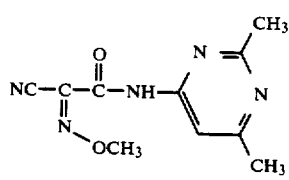

3.5 g (0.03 mol) of isoamyl nitrite and then 2 g (0.03 mol) of sodium ethylate in 15 ml of ethanol are added to a solution of 5.7 g (0.03 mol) of 2,6-dimethyl-4-cyanoacetamido-pyrimidine in 30 ml of ethanol, and the mixture is allowed to stand at 25° C. for 30 minutes. 3.8 g (0.03 mol) of dimethyl sulphate are then added, and the mixture is allowed to stand at room temperature for a further hour. After removing the solvent by distillation in vacuo, the residue is chromatographed using ethyl acetate as eluent.

2.3 g (33% of theory) of 2,6-dimethyl-4-(2-cyano-2-methoximino-acetamido)-pyrimidine of melting point 128° C. are obtained.

Preparation of the starting compound

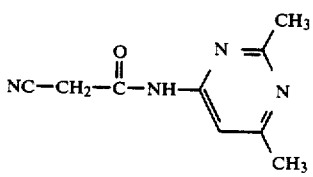

6.9 g (0.08 mol) of cyanoacetic acid and 10 g (0.08 mol) of 4-amino-2,6-dimethylpyrimidine are dissolved in 80 ml of pyridine, and 8.3 g (0.08 mol) of acetic anhydride are added. The pyridine is subsequently removed in vacuo, and the residue is taken up in toluene, concentrated, taken up a second time in toluene and again concentrated. The residue is chromatographed using ethyl acetate as eluent.

7.8 g (50.5% of theory) of 2,6-dimethyl-4-cyanoacetamido-pyrimidine of melting point 178° C. are obtained.

EXAMPLE 3

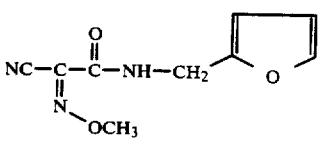

3.4 g (0.05 mol) of sodium ethylate in 25 ml of ethanol are added to 8.2 g (0.05 mol) of 2-(cyanoacetamidomethyl)-furan and 5.9 g (0.05 mol) of isoamyl nitrite in 25 ml of ethanol, and the reaction mixture is allowed to stand at room temperature for one hour. 6.3 g (0.05 mol) of dimethyl sulphate are then added, and the mixture is allowed to stand at room temperature for a further 12 hours. After removing the solvent by distillation, the residue is chromatographed using ethyl acetate as eluent.

8.7 g (87% of theory) of 2-(2-methoximino-cyanoacetamidomethyl)-furan are obtained as an oil.

$^1$H NMR (CDCl$_3$): δ=4.25 (s); 4.52 (d); 6.31; 6.35; 6.97 (broad); 7.38 ppm.

Preparation of the starting compound

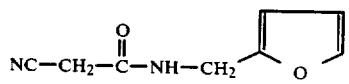

5.8 g (0.05 mol) of methanesulphonyl chloride in 25 ml of pyridine are added to a solution of 4.9 g (0.05 mol) of 2-furfurylamine and 4.3 g (0.05 mol) of cyanoacetic acid in 25 ml of pyridine, the pyridine is then removed by distillation in vacuo, 25 ml of toluene are added to the residue, the mixture is concentrated in vacuo, a second portion of 25 ml of toluene is added, the mixture is again concentrated in vacuo, and the residue is treated with 50 ml of water, filtered off under suction, washed twice with 20 ml of water in each case and dried.

4.5 g (55% of theory) of 2-(cyanoacetamidomethyl)-furan of melting point 93°–95° C. are obtained.

EXAMPLE 4

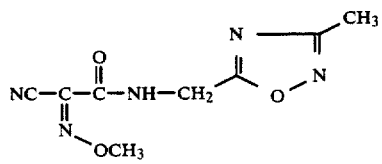

Firstly, 10.42 g (0.089 mol) of isopentyl nitrite and subsequently 6.0 g (0.089 mol) of sodium ethylate in 50 ml of absolute ethanol are added dropwise with stirring to 16 g (0.089 mol) of 5-cyanoacetamidomethyl-3-methyl-1,2,4-oxadiazole in 80 ml of absolute ethanol at room temperature. The mixture is stirred at room temperature for a further hour, 11.22 g (0.089 mol) of dimethyl sulphate are then added dropwise, and the mixture is stirred for a further hour at room temperature. For work-up, the solvent is removed in vacuo, the residue is taken up in dichloromethane, washed several times with water and dried over sodium sulphate, the solvent is removed in vacuo, and the residue is purified chromatographically on silica gel (eluent: dichloromethane/ether 10:1).

8.2 g (41% of theory) of 5-(2-cyano-2-methoximinoacetamidomethyl)-3-methyl-1,2,4-oxadiazole of melting point 69° C. are obtained.

Preparation of the starting compound

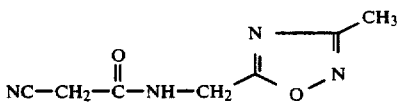

6.8 g (0.067 mol) of triethylamine are added to 10.0 g (0.067 mol) of 5-aminomethyl-3-methyl-1,2,4-oxadiazole in 300 ml of absolute tetrahydrofuran. The mixture is stirred at room temperature for about 15 minutes, and 3.47 g (0.00335 mol) of cyanoacetyl chloride are subsequently added with cooling in an ice bath, the mixture is stirred for about 5 minutes, 3.4 g (0.00336 mol) of triethylamine are added, and a total of 6.93 g (0.067 mol) of cyanoacetyl chloride and 6.8 g (0.067 mol) of triethylamine are subsequently added alternately in an iterative process. For work-up, the precipitated triethylamine hydrochloride is filtered off, the solvent is evaporated off in vacuo, and the brown, oily residue is further reacted in crude form.

12.0 g (99.5% of theory) of 5-cyanoacetamidomethyl-3-methyl-1,2,4-oxadiazole are obtained.

The following 2-cyano-2-alkoximino-acetamides of the general formula (I) are obtained in a corresponding fashion and according to the general instructions for the preparation:

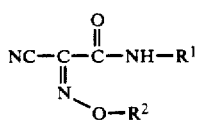

(I)

| Example No. | R$^1$ | R$^2$ | Physical properties |
|---|---|---|---|
| 5 | ![pyridyl-2-CH2-] | —CH$_3$ | m.p. 136°–137° C. |
| 6 | ![pyridyl-3-CH2-] | —CH$_3$ | m.p. 85°–88° C. |
| 7 | ![pyridyl-4-CH2-] | —CH$_3$ | m.p. 135°–139° C. |
| 8 | ![pyridyl-3-CH2-] | —CH$_2$—phenyl | m.p. 90°–92° C. |

-continued
| Example No. | R¹ | R² | Physical properties |
|---|---|---|---|
| 9 | 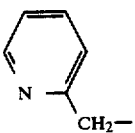 | —CH₂—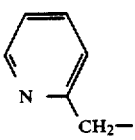—CH₃ | m.p. 94°–95° C. |
| 10 | 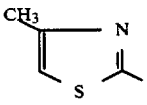 | —(CH₂)₁₁—CH₃ | m.p. 50° C. |
| 11 | 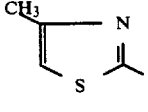 | —CH₃ | m.p. 53°–54° C. |
| 12 | 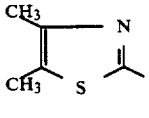 | —CH₂—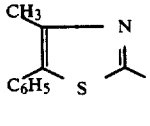 | m.p. 98° C. |
| 13 | 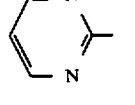 | —CH₃ | m.p. 117° C. |
| 14 | 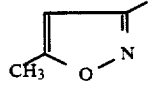 | —CH₃ | m.p. 180° C. |
| 15 | 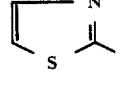 | —CH₃ | m.p. 138° C. |
| 16 | 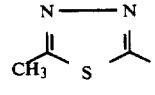 | —CH₂—CN | m.p. 182° C. |
| 17 | 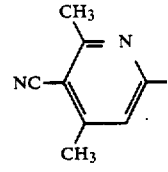 | —CH₃ | m.p. 220° C. (Decomp.) |
| 18 | 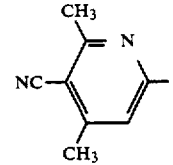 | —CH₃ | m.p. 210° C. |
| 19 |  | —CH₃ | m.p. 196° C. |
| 20 |  | —CH₂—CN | m.p. 218° C. |

-continued

| Example No. | R¹ | R² | Physical properties |
|---|---|---|---|
| 21 | 1,3,4-thiadiazol-2-yl | —CH₂—CN | m.p. 162° C. |
| 22 | 1H-benzimidazol-2-yl | —CH₃ | m.p. 172° C. |
| 23 | 5-methyl-1,3,4-thiadiazol-2-yl (3-methyl) | —CH₂—CN | m.p. 228° C. (Decomp.) |
| 24 | 5-methyl-1,3,4-thiadiazol-2-yl (3-methyl) | —CH₂—C₆H₅ | m.p. 228° C. (Decomp.) |
| 25 | 3,5-dimethylisoxazol-4-yl | —CH₂—C₆H₅ | m.p. 164° C. |
| 26 | 2,6-dimethylpyrimidin-4-yl | —CH₃ | m.p. 120°–125° C. |
| 27 | pyridin-2-yl | —CH₃ | m.p. 105°–110° C. |
| 28 | pyridin-3-yl | —CH₃ | m.p. 142°–143° C. |
| 29 | 5-chloro-6-methylpyridin-2-yl | —CH₃ | m.p. 139°–142° C. |
| 30 | 2-chloropyridin-3-yl | —CH₃ | m.p. 113°–115° C. |
| 31 | 3,5-dichloro-6-methylpyridin-2-yl | —CH₃ | m.p. 142°–143° C. |

-continued

| Example No. | R¹ | R² | Physical properties |
|---|---|---|---|
| 32 | 4-methylpyridin-2-yl (=N, CH₃ at 4-position) | —CH₃ | m.p. 124°–130° C. |
| 33 | thiophen-2-yl-CH₂— | —CH₃ | NMR*: 4.23, 4.7 |
| 34 | 6-methylpyridin-2-yl (CH₃ at 2-position of pyridine, with =N) | —CH₃ | m.p. 115°–117° C. |
| 35 | 2-methylquinolin-4-yl | —CH₃ | m.p. 187°–191° C. |
| 36 | N=C(CH₃)–S attached to 2-methylphenyl (benzothiazoline-type) | —CH₃ | m.p. 215°–218° C. |
| 37 | 3-methylpyridin-2-yl | —CH₃ | NMR*: 2.18, 4.27 |
| 38 | 4-ethoxy substituted benzothiazoline (C₂H₅O–phenyl with N=C(CH₃)–S) | —CH₃ | NMR*: 1.38, 4.28 |
| 39 | 2-chloro substituted benzothiazoline (Cl–phenyl with N=C(CH₃)–S) | —CH₃ | NMR*: 4.28 |
| 40 | 4,6-dimethoxypyrimidin-2-yl (CH₃O, N, N, CH₃O) | —CH₃ | m.p. 140°–142° C. |

-continued

| Example No. | R¹ | R² | Physical properties |
|---|---|---|---|
| 41 | 4,6-dimethoxypyrimidin-2-yl (CH₃O at 4 and 6) | —CH₂—C₆H₅ | m.p. 112°–113° C. |
| 42 | 4-ethoxy-2-(S-) benzothiazol-like (C₂H₅O-phenyl with S, N=) | —CH₂—C₆H₅ | m.p. 139°–140° C. |
| 43 | 4-methoxy-phenyl with S, N= | —CH₃ | NMR*: 3.83, 4.28 |
| 44 | 4-methoxy-6-methyl-pyrimidin-2-yl | —CH₃ | m.p. 163°–165° C. |
| 45 | pyridin-2-yl | —CH₂—C₆H₅ | m.p. 84° C.–85° C. |
| 46 | 4-methoxy-phenyl with S, N= | —CH₂—C₆H₅ | NMR*: 3.83, 5.5 |
| 47 | 4-methoxy-6-methyl-pyrimidin-2-yl | —CH₂—C₆H₅ | NMR*: 3.95, 5.5 |
| 48 | 4,6-diethoxy-1,3,5-triazin-2-yl | —CH₃ | NMR*: 4.32, 4.52 |
| 49 | 6-methylpyridin-2-yl | —CH₂—C₆H₅ | m.p. 121°–123° C. |

-continued

| Example No. | $R^1$ | $R^2$ | Physical properties |
|---|---|---|---|
| 50 | CH₃-pyridin-2-yl (6-methylpyridin-2-yl) | —CH₂—CN | m.p. 125° C. |
| 51 | 6-methylpyridin-2-yl | —C₂H₅ | NMR*: 2.45, 4.57 |
| 52 | 4,5-dimethylthiazol-2-yl (CH₃, CH₃ on thiazole) | —C₂H₅ | m.p. 140°–141° C. |
| 53 | 4,5-dimethylthiazol-2-yl | —(CH₂)₁₁—CH₃ | NMR*: 0.88, 3.43 |
| 54 | HO—(CH₂)₃— | —C₂H₅ | NMR*: 1.42, 4.48 |
| 55 | HO—(CH₂)₃— | —CH₂—C₆H₅ | NMR*: 3.69, 5.38 |
| 56 | HO—(CH₂)₃— | —(CH₂)₂—CH₃ | NMR*: 3.75, 4.41 |
| 57 | HO—(CH₂)₃— | —(CH₂)₁₁—CH₃ | NMR*: 3.72, 4.42 |
| 58 | HO—(CH₂)₃— | —(CH₂)₂—O—C(=O)—CH₃ | NMR*: 2.09, 3.73 |
| 59 | HO—(CH₂)₃— | —CH(CH₃)—C(=O)—CH₃ | NMR*: 3.77, 4.9 |
| 60 | HO—(CH₂)₃— | —CH₂—C(=O)—O—C₂H₅ | NMR*: 3.72, 4.95 |
| 61 | HO—(CH₂)₃— | —CH₂—CH=CH—CH₃ | NMR*: 3.72, 4.85 |
| 62 | HO—(CH₂)₃— | —CH₂—CH=CH₂ | NMR*: 3.74, 4.9 |
| 63 | HO—(CH₂)₃— | —CH₂—CH=C(Cl)(CH₃) | NMR*: 3.73, 2.2 |
| 64 | HO—(CH₂)₃— | —CH₂—C≡CH | NMR*: 2.71, 3.72, 5.0 |
| 65 | HO—(CH₂)₃— | —(CH₂)₂—CH=CH₂ | NMR*: 3.73, 4.48 |
| 66 | HO—(CH₂)₃— | —CH₂—(4-Cl-C₆H₄) | m.p. 90° C. |
| 67 | HO—(CH₂)₃— | —CH₂—(4-CH₃-C₆H₄) | NMR*: 3.7, 5.34 |

-continued

| Example No. | R¹ | R² | Physical properties |
|---|---|---|---|
| 68 | HO—(CH$_2$)$_3$— | —CH$_2$—(3,4-dichlorophenyl) | m.p. 94°–95° C. |
| 69 | HO—(CH$_2$)$_2$— | —C$_2$H$_5$ | NMR*: 3.78, 4.5 |
| 70 | HO—(CH$_2$)$_2$— | —(CH$_2$)$_2$—CH$_3$ | NMR*: 3.78, 4.41 |
| 71 | HO—(CH$_2$)$_2$— | —(CH$_2$)$_{11}$—CH$_3$ | NMR*: 3.8, 4.43 |
| 72 | HO—(CH$_2$)$_2$— | —CH(CH$_3$)—C(O)—CH$_3$ | NMR*: 3.82, 4.92 |
| 73 | HO—(CH$_2$)$_2$— | —CH$_2$—C(O)—CH$_3$ | NMR*: 3.8 |
| 74 | HO—(CH$_2$)$_2$— | —CH$_2$—C(O)—O—C$_2$H$_5$ | NMR*: 3.75, 4.92 |
| 75 | HO—(CH$_2$)$_2$— | —(CH$_2$)$_2$—O—C(O)—CH$_3$ | NMR*: 2.12, 3.78 |
| 76 | HO—(CH$_2$)$_2$— | —CH$_2$—CH=CH$_2$ | NMR*: 3.77, 4.91 |
| 77 | HO—(CH$_2$)$_2$— | —CH$_2$—CH=CH—CH$_3$ | NMR*: 1.75, 3.8 |
| 78 | HO—(CH$_2$)$_2$— | —CH$_2$—CH=C(Cl)(CH$_3$) | NMR*: 2.21, 3.78 |
| 79 | HO—(CH$_2$)$_2$— | —CH$_2$—C≡CH | NMR*: 2.65, 3.72 |
| 80 | HO—(CH$_2$)$_2$— | —(CH$_2$)$_2$—CH=CH$_2$ | NMR*: 3.79, 4.5 |
| 81 | HO—(CH$_2$)$_2$— | —CH$_2$—(4-chlorophenyl) | m.p. 112°–114° C. |
| 82 | HO—(CH$_2$)$_2$— | —CH$_2$—(4-methylphenyl) | m.p. 100° C. |
| 83 | HO—(CH$_2$)$_2$— | —CH$_2$—(2-chlorophenyl) | m.p. 98°–103° C. |
| 84 | HO—(CH$_2$)$_2$— | —CH$_2$—(3,4-dichlorophenyl) | m.p. 120°–121° C. |
| 85 | HO—(CH$_2$)$_2$— | —CH$_2$—phenyl | NMR*: 3.77, 5.42 |

EXAMPLE 2

Preparation of 2-benzylthio-5,7-dimethyl-1,2,4-triazolo[1,5-a]pyrimidine

Twenty percent NaOH (14.0 g, 70 mmol) was added dropwise to a suspension of 11.5 g (64.0 mmol) of the mercaptan prepared in Example 1 in 125 ml of $H_2O$ over about 5 minutes. Benzyl chloride (7.4 ml, 8.1 g, 64 mmol) in 20 ml of $CH_3OH$ was added and the resulting mixture was vigorusly stirred at room temperature for 24 hours. The solid which began separating shortly after the addition of benzyl chloride was collected by filtration and dried in vacuo to afford 16.1 g of white solid, m.p. 134°-135° C. (lit m.p. 132°-134° C., T. Novinson et al, *J. Med. Chem.*, 25, 420 (1982)): $^1H$ NMR ($CDCl_3$) δ 7.1–7.6 (5H, m, Ph), 6.63 (1H, s, H in 6-position), 4.50 (2H, s, $-CH_2S-$), 2.67 and 2.58 (3H each, s, $CH_3$ groups in 5- and 7-positions); IR ($CHCl_3$) 1620, 1447, 1339 and 1295 $cm^{-1}$. 93% yield.

Analysis:
Calculated for $C_{14}H_{14}N_4S$: C, 62.20; H, 5.22; N, 20.72.
Found: C, 62.21; H, 5.14; N, 20.89.

EXAMPLE 3

Preparation of 2-benzylthio-6,7-cyclopentano-5-methyl-1,2,4-triazolo[1,5-a]pyrimidine A solution of 51.6 g (0.250 mol) of 3-amino-5-benzylthio-1,2,4-triazole and 31.5 g (0.250 mol) of 2-acetylcyclopentanone in 600 ml of HOAc was heated at reflux for 9.5 hours. The solvent was removed by evaporation, and the brown solid residue was recrystallized from EtOH to yield a light brown solid. A second recrystallization from EtOH gave 45.4 g (61 percent) of the desired product as a light brown solid, m.p. 157°-158.5° C.: $^1H$ NMR ($CDCl_3$) δ7.0–7.6 (5H, m), 4.51 (2H, s), 3.29 (2H, t), 2.97 (2H, t), 2.0–2.7 (5H, m including s at 2.52); IR ($CHCl_3$) 1621, 1343 and 1290 $cm^{-1}$.

Analysis:
Calculated for $C_{16}H_{16}N_4S$: C, 64.84; H, 5.44, N, 18.90; S, 10.82.
Found: C, 64.88; H, 5.47; N, 18.98; S, 10.72.

EXAMPLE 4

Preparation of 2-benzylthio-5,6,7-trimethyl-1,2,4-triazolo[1,5-a]pyrimidine

A solution of 51.6 g (0.250 mol) of 3-amino-5-benzylthio-1,2,4-triazole and 28.5 g (0.250 mol) of 3-methyl-2,4-pentanedione in 350 ml of glacial acetic acid was heated at reflux for 17 hours. Upo cooling to room temperature, the reaction mixture was poured onto ice. The pale yellow solid which separated was collected by filtration, washed with water and dried in vacuo to yield 67.1 g (94%) of the desired product as a pale yellow solid, m.p. 133.5°-135° C. The IR and $^1H$ NMR spectra were consistent with the assigned structure.

Analysis:
Calculated for $C_{15}H_{15}N_4S$: C, 63.35; H, 5.67; N, 19.70; S, 11.27.
Found: C, 63.07; H, 5.48; N, 19.71; S, 11.09.

EXAMPLE 5

Preparation of 2-benzylthio-6-chloro-1,2,4-triazolo[1,5-a]pyrimidine

A solution of 6.52 g (31.6 mmol) of 3-amino-5-benzylthio-1,2,4-triazole and 9.09 g (31.6 mmol) of 1,3-bis(-dimethylamino)-2-chlorotrimethinium perchlorate in 100 ml of glacial acetic acid was heated at reflux for 19 hours. After cooling to room temperature, the solution was poured into 300 ml of water. The solid which separated was collected by filtration, washed with water and dried in vacuo to yield 4.12 g (48%) of the desired product as a brown solid, m.p. 119.5°-135° C. (decomposition). IR and $^1H$ NMR spectra were consistent with the assigned structure.

Analysis:
Calculated for $C_{12}H_9ClN_4S$: C, 51.90; H, 3.20; N, 20.24.
Found: C, 51.87; H, 3.42; N, 19.81.

EXAMPLE 6

Preparation of 2-benzylthio-1,2,4-triazolo-[1,5-a]pyrimidine

A solution of 2.0 g (9.6 mmol) of 3-amino-5-benzylthio-1,2,4-triazole and 2.3 ml (9.6 mmol) of malonaldehyde bis(diethylacetal) in 20 ml of glacial acetic acid was heated at reflux for 17 hours. After cooling to room temperature, the solvent was removed by evaporation at reduced pressure. The brown solid residue was recrystallized from isopropyl alcohol to afford 0.4 g (17%) of the desired product as a light brown crystalline solid, m.p. 104°-106° C. IR and $^1H$ NMR spectra were consistent with the assigned structure.

Analysis:
Calculated for $C_{12}H_{10}N_4S$: C, 59.52; H, 4.13; N, 23.13.
Found: C, 59.19; H, 4.09; N, 22.73.

EXAMPLE 7

Preparation of 2-benzylthio-5-methyl-1,2,4-triazolo[1,5-a]pyrimidine

A solution of sodium ethoxide in EtOH was prepared by dissolving 0.54 g (24 mg-atoms) of sodium metal in 120 ml of anhydrous EtOH, and 10.0 g (48 mmol) of 3-amino-5-benzylthio-1,2,4-triazole was added. After stirring for 15 minutes at room temperature, 6.4 ml (6.35 g, 48.4 mmol) of acetylacetaldehyde dimethyl acetal dissolved in 100 ml of absolute EtOH was was added dropwise. After the addition was complete the reaction mixture was stirred at room temperature for 68 hours. The product which separated from solution was collected by filtration and dried to give 10.1 g (83%) of tan solid, m.p. 128.5°-130° C. IR and $^1H$ NMR spectra were in agreement with the assigned structure.

Analysis:
Calculated for $C_{13}H_{12}N_4S$: C, 60.94; H, 4.68; N, 21.86.
Found: C, 60.69; H, 4.61; N, 21.85.

EXAMPLE 8

Preparation of 2-benzylthio-5-hydroxy-7-methyl-1,2,4-triazolo[1,5-a]pyrimidine Ethyl 2,3-dibromobutyrate (1.33 g, 48.5 mmol) was added dropwise over 15 minutes to a solution of 10 g (49 mmol) of 3-amino-5-benzylthio-1,2,4-triazole in 20 ml of pyridine heated to 65° C. After the addition was complete, the reaction mixture was heated at 65° C. for 20 hours, cooled to room temperature and filtered. The filtrate was concentrated by evaporation at reduced pressure. The residue was triturated with methanol to separate 1.64 g (13%) of the desired product as a colorless crystalline solid, m.p. 219°–220° C. IR and $^1$H NMR spectra were in agreement with the assigned structure.
Analysis:
Calculated for $C_{13}H_{12}N_4OS$: C, 57.37; H, 4.41; N, 20.60.
Found: C, 56.86; H, 4.41; N, 20.72.

EXAMPLE 9

Preparation of
2-benzylthio-5-methoxy-7-methyl-1,2,4-triazolo[1,5-a]pyrimidine

A solution of 2.67 g (9.80 mmol) of 2-benzylthio-5-hydroxy-7-methyl-1,2,4-triazolo[1,5-a]pyrimidine in 50 ml of phosphorous oxychloride was heated at reflux for 3 hours. The excess phosphorous oxychloride was removed by evaporation at reduced pressure. The residue was partitioned between $CH_2Cl_2$ and cold water. The organic phase was separated, dried ($MgSO_4$) and concentrated by evaporation at reduced pressure. The resulting solid was added to 50 ml (0.22 mol) of a 25 weight percent solution of sodium methoxide in methanol. The resulting suspension was stirred at room temperature for 30 minutes, diluted with 50 ml of water and filtered. The solid collected was dried in vacuo to yield 1.41 g (41%) of the desired product as a light brown solid, m.p. 112.5°–115° C. IR and $^1$H NMR spectra were consistent with the assigned structure.

EXAMPLE 10

Preparation of
2-benzylthio-7-methyl-1,2,4-triazolo[1,5-a]pyrimidine

A solution of 50 g (0.24 mol) of 3-amino-5-benzylthio-1,2,4-triazole in 500 ml of glacial acetic acid was added dropwise over 3–4 hours to a solution of 34.0 g (0.25 mol) of acetylacetaldehyde dimethyl acetal in 500 ml of glacial acetic acid heated at 100° C. After the addition was complete the reaction mixture was heated at reflux overnight, cooled to room temperature and poured into an ice-water mixture. The solid which separated was collected by filtration and recrystallized from ethanol to yield 27 g (41%) of the desired product as a solid, m.p. 102°–104° C. IR and $^1$H NMR spectra were in agreement with the assigned structure.
Analysis:
Calculated for $C_{13}H_{12}N_4S$: C, 60.94; H, 4.68; N, 21.85.
Found: C, 60.81; H, 4.68; N, 21.74.

EXAMPLE 11

Preparation of
2-benzylthio-6-methyl-1,2,4-triazolo[1,5-a]pyrimidine

A suspension of 14.4 g (0.124 mol) of 3-amino-5-benzyl-1,2,4-triazole and 30.0 g (0.124 mol) of 1,3-bis(dimethylamino)-2-methyltrimethinium perchlorate in 500 ml of glacial acetic acid was heated at reflux for 63 hours. The reaction mixture was subjected to the work-up described in Example 5 to yield 13.9 g (68%) of the desired product as a brown solid, m.p. 254°–256° C. IR and $^1$H NMR spectra were in agreement with the assigned structure.
Analysis:
Calculated for $C_6H_6N_4S$: C, 43.35; H, 3.61; N, 33.72
Found: C, 42.71; H, 3.49; N, 33.26.

EXAMPLE 12

Preparation of
2-benzylthio-6-chloro-5,7-dimethyl-1,2,4-triazolo[1,5-a]pyrimidine To a suspension of 153 g (0.74 mol) 3-amino-5-benzylthio-1,2,4-triazole in 250 ml of glacial acetic acid was added 100 g (0.74 mol) of 3-chloro-2,4-pentanedione in a dropwise manner. The reaction mixture was heated at reflux for 18 hours and cooled to room temperature. The reaction mixture was poured over ice and the oil which separated solidified upon stirring. The solid was collected by filtration and recrystallized from methanol to yield 116 g (79%) of the desired product as an off white solid, m.p. 164°–166° C. IR and $^1$H NMR spectra were in agreement with the assigned structure.
Analysis:
Calculated for $C_{14}H_{13}ClN_4S$: C, 55.16; H, 4.30; N, 18.38.
Found: C, 55.11; H, 4.30; N, 18.34.

EXAMPLE 13

Preparation of
2-benzylthio-6-ethoxy-1,2,4-triazolo[1,5-a]pyrimidine

This material was prepared in 28% yield from 3-amino-5-benzylthio-1,2,4-triazole and 1,3-bis(dimethylamino)-2-ethoxytrimethinium perchlorate following the general procedure described in Example 5. The desired product was isolated as a solid, m.p. 139°–140° C. IR and $^1$H NMR spectra were in agreement with the assigned structure.
Analysis:
Calculated for $C_{14}H_{14}N_4OS$: C, 58.73; H, 4.89; N, 19.57.
Found: C, 58.68; H, 4.64; N, 19.58.

EXAMPLE 14

Preparation of
2-benzylthio-2-benzylthio-5-isopropyl-1,2,4-triazolo[1,5-a]pyrimidine This material was prepared in 96% yield from 3-amino-5-benzylthio-1,2,4-triazole and 4-methyl-3-oxopentanal following the general procedure described in Example 7. The desired product was isolated as a solid, m.p. 65°–66° C. IR and $^1$H NMR were in agreement with the assigned structure.
Analysis:
Calculated for $C_{15}H_{16}N_4S$: C, 63.36; H, 5.63; N, 19.71.
Found: C, 63.00; H, 5.62; N, 19.62.

EXAMPLE 15

Preparation of
2-benzylthio-5,6-dimethyl-1,2,4-triazolo[1,5-a]pyrimidine

A solution of 5.0 g (24 mmol) of 3-amino-5-benzylthio-1,2,4-triazole and 5.0 g (41 mmol) of the sodium salt of 2-methyl-3-oxobutanal in 200 ml of glacial acetic acid was heated at reflux overnight. The solution was cooled to room temperature and the reaction mixture was concentrated by evaporation at reduced pressure. The residue was combined with ice and $H_2O$ to separate a tan solid. The solid was collected by filtration, dried and carefully recrystallized from ethyl acetate to yield 3.53 g (54%) of the desired product as a crystalline solid, m.p. 147°–149° C. IR and $^1$H NMR spectra were in agreement with the assigned structure.
Analysis:

Calculated for $C_{14}H_{14}N_4S$: C, 62.10; H, 5.18; N, 20.72.
Found: C, 61.58; H, 5.18; N, 20.45.

EXAMPLE 16

Preparation of
2-benzylthio-6-chloro-7-hydroxy-5-methyl-1,2,4-triazolo[1,5-a]pyrimidine A solution of 16 g (77 mmol) of 3-amino-5-benzylthio-1,2,4-triazole and 10.6 g (77 mmol) of ethyl 2-chloroacetoacetate in 150 ml of glacial acetic acid was heated at 100° C. for 17 hours. Upon cooling to room temperature the solid which separated was collected by filtration. The filtrate was diluted with ice water to separate an additional quantity of solid. The solids were combined and dried to yield 14.0 g (60% of the desired product as a solid, m.p. 258°–260° C. IR and $^1$H NMR were in agreement with the assigned structure.
Analysis:
Calculated for $C_{13}H_{11}ClN_4OS$: C, 50.89; H, 3.58; N, 18.27.
Found: C, 50.51; H, 3.36; N, 18.67.

EXAMPLE 17

Preparation of
2-benzylthio-6,7-dichloro-5-methyl-1,2,4-triazolo[1,5-a]pyrimidine This material was prepared in 68% yield from 2-benzylthio-6-chloro-7-hydroxy-5-methyl-1,2,4-triazolo[1,5-a]pyrimidine and phosphorus oxychloride following the general procedure described in Example 20. The desired product was isolated as a solid, m.p. 103°–105° C. IR and $^1$H NMR spectra were in agreement with the assigned structure.
Analysis:
Calculated for $C_{13}H_{10}Cl_2N_4S$: C, 48.00; H, 3.07; N, 17.23.
Found: C, 47.40; H, 3.00; N, 17.43.

EXAMPLE 18

Preparation of
2-benzylthio-6-chloro-5-methyl-1,2,4-triazolo[1,5-a]pyrimidine

This material was prepared by reduction of 2-benzylthio-6,7-dichloro-5-methyl-1,2,4-triazolo[1,5-a]pyrimidine with zinc-copper couple following the general procedure described in Example 21. The desired product was isolated in 88% yield as a solid, m.p. 160°–161° C. IR and $^1$H NMR spectra were in agreement with the assigned structure.
Analysis:
Calculated for $C_{13}H_{11}ClN_4S$: C, 53.56; H, 3.56; N, 19.27.
Found: C, 53.30; H, 3.79; N, 19.28.

EXAMPLE 19

Preparation of
2-benzylthio-5,7-dihydroxy-1,2,4-triazolo[1,5-a]pyrimidine

A solution of 125 g (0.58 mol) of a 25% solution of sodium methoxide in methanol dissolved in 100 ml of absolute ethanol was treated with 66.3 ml (0.29 mol) of dimethyl malonate followed by 60.0 g (0.20 mol) of 3-amino-5-benzylthio-1,2,4-triazole. The resulting solution was heated at reflux for 5 days. On cooling to room temperature the solid which had separated was collected by filtration, washed with cold ethanol and dissolved in 1000 ml of water. The resulting yellow solution was acidified with concentrated HCl to precipitate a solid. The solid was collected by filtration and dried to yield 70.1 g (82%) of the desired product as a white solid, m.p. 199°–210° C. (decomposition). IR and $^1$H NMR spectra were in agreement with the assigned structure.
Analysis:
Calculated for $C_{12}H_{10}N_4O_2S \cdot H_2O$: C, 49.30; H, 4.14, N, 19.16.
Found: C, 48.70; H, 3.89; N, 18.83.

EXAMPLE 20

Preparation of
2-benzylthio-5,7-dichloro-1,2,4-triazolo[1,5-a]pyrimidine

A suspension of 70.0 g (0.24 mol) of 2-benzylthio-5,7-dihydroxy-1,2,4-triazolo[1,5-a]pyrimidine and 67.0 ml (0.72 mol) of phosphorous oxychloride in 600 ml of acetonitrile was heated at reflux for 3 hours. The resulting orange solution was stirred at room temperature overnight (17 hours). The solution was filtered and the filtrate was concentrated by evaportion at reduced pressure. The residue was partitioned between cold water and methylene chloride, and the organic phase was separated and dried (MgSO$_4$). The organic phase was concentrated to induce crystallization. The desired product was collected by filtration to yield 98.0 g (81%) of solid, m.p. 97°–100° C. IR and $^1$H NMR spectra were in agreement with the assigned structure.
Analysis:
Calculated for $C_{12}H_8Cl_2N_4S$: C, 46.32; H, 2.59; N, 18.00.
Found: C, 46.43; H, 2.57; N, 18.08.

EXAMPLE 21

Preparation of
2-benzylthio-5-chloro-1,2,4-triazolo[1,5-a]pyrimidine

A zinc-copper couple was prepared following the precedure of Bradley (J. Org. Chem. 31, 626 (1966)) by stirring 1.0 g of copper sulfate in 20 ml of water with 15.0 g of zinc dust for 2 hours. The couple was collected by filtration, washed with acetone and dried overnight under vacuum at 100° C. To a solution of 33.0 g (106 mmol) of 2-benzylthio-5,7-dichloro-1,2,4-triazolo[1,5-a]pyrimidine in 12.5 ml (213 mmol) of acetic acid, 50 ml of methanol and 300 ml of tetrahydrofuran was added 20.5 g of Zn-Cu couple. The mixture was stirred overnight at 22°–23° C. When the reaction was complete (TLC analysis) the reaction mixture was filtered through celite and the filtrate was concentrated by evaporation at reduced pressure. The residue was triturated with hexane to separate a solid. The solid was collected by filtration to yield the desired product as 26.5 g (92%) of orange solid, m.p. 125°–127° C. IR and $^1$H NMR spectra were in agreement with the assigned structure.
Analysis:
Calculated for $C_{12}H_9ClN_4S$: C, 52.08; H, 3.25; N, 20.25.
Found: C, 51.76; H, 3.00; N, 20.27.

EXAMPLE 22

Preparation of
2-benzylthio-5-methoxy-1,2,4-triazolo[1,5-a]pyrimidine

A mixture of 6.0 g (22 mmol) of 2-benzylthio-5-chloro-1,2,4-triazolo[1,5-a]pyrimidine in 25 ml of methanol was treated with 5.0 g (23.8 mmol) of a 25% solution of sodium methoxide in methanol. After stirring for 1.5 hours the reaction mixture was diluted with 100 ml of water and neutralized with 3N HCL (aq). The solid which separated was collected by filtration, washed with water and dried to afford 5.0 g (84%) of the desired product as a white solid, m.p. 126°–128° C. IR and ¹H NMR spectra were in agreement with the assigned structure.

Analysis:

Calculated for $C_{13}H_{12}N_4OS$: C, 57.34; H, 4.41; N, 20.58.
Found: C, 57.21; H, 4.42; N, 20.13.

EXAMPLE 23

Preparation of 2-benzylthio-5-(2,2,2-trifluoroethoxy)-1,2,4-triazolo[1,5-a]pyrimidine A solution of sodium 2,2,2-trifluoroethoxide in tetrahydrofuran was prepared by the addition of 1.1 g (48 mg-atom) of sodium metal to a solution of 3.5 ml (48 mmol) of 2,2,2-trifluoroethanol in 100 ml of tetrahydrofuran. To this solution was added 7.0 g (25 mmol) of 2-benzylthio-5-chloro-1,2,4-triazolo[1,5-a]pyrimidine, and the reaction mixture was stirred for 30 minutes and concentrated by evaporation at reduced pressure to approximately one quarter of the original volume. Pentane (200 ml) was added to induce crystallization. The solid which separated was collected by filtration to yield 6.42 g (75%) of the desired product as a light yellow solid, m.p. 114°–118° C. IR and ¹H NMR spectra were in agreement with the assigned structure.

Analysis:

Calculated for $C_{14}H_{11}F_3N_4OS$: C, 49.40; H, 3.23; N, 16.46.
Found: C, 49.63; H, 3.09; N, 16.70.

EXAMPLE 24

Preparation of 2-benzylthio-5-ethoxy-1,2,4-triazolo[1,5-a]pyrimidine

This material was prepared by heating 2 benzylthio-5-(2,2,2-trifluoroethoxy)-1,2,4-triazolo[1,5-a]pyrimidine in boiling ethanol. The hot mixture was filtered and the filtrate was concentrated. The crude product was recrystallized from isopropanol to yield the desired product as a solid, m.p. 115°–117° C. IR and ¹H NMR spectra were in agreement with the assigned structure.

Analysis:

Calculated for $C_{14}H_{14}N_4OS$: C, 58.73; H, 4.89; N, 19.31; S, 11.20.
Found: C, 57.90; H, 4.69; N, 19.30; S, 10.79.

EXAMPLE 25

Preparation of 2-benzylthio-5,7-dihydroxy-6-methyl-1,2,4-triazolo[1,5-a]pyrimidine This material was prepared in 80% yield from 3-amino-5-benzylthio-1,2,4-triazole and dimethyl 2-methyl malonate following the general procedure described in Example 19. The product was isolated as a solid, m.p. 260°–272° C. (decomposition). IR and ¹H NMR spectra were in agreement with the assigned structure.

Analysis:

Calculated for $C_{13}H_{12}N_4O_2S$: C, 54.15; H, 4.16; N, 19.44.
Found: C, 53.48; H, 4.07; N, 19.53.

EXAMPLE 26

Preparation of 2-benzylthio-5,7-dichloro-6-methyl-1,2,4-triazolo[1,5-a]pyrimidine This material was prepared in 97% yield from the reaction of 2-benzylthio-5,7-dihydroxy-6-methyl-1,2,4-triazolo[1,5-a]pyrimidine and phosphorous oxychloride following the general procedure described in Example 20. The product was isolated as a solid, m.p. 121°–123° C. IR and ¹H NMR spectra were in agreement with the assigned structure.

Analysis:

Calculated for $C_{13}H_{10}Cl_2N_4S$: C, 48.01; H, 3.08; N, 17.23.
Found: C, 47.65; H, 3.11; N, 17.70.

EXAMPLE 27

Preparation of 2-benzylthio-5-chloro-6-methyl-1,2,4-triazolo[1,5-a]pyrimidine

This material was prepared in 32% yield by reduction of 2-benzylthio-5,7-dichloro-6-methyl-1,2,4-trizolo[1,5-a]pyrimidine with zinc-copper couple following the general procedure described in Example 21. The desired product was isolated as a solid, m.p. 179°–181° C. IR and ¹H NMR spectra were in agreement with the assigned structure.

Analysis:

Calculated for $C_{13}H_{11}ClN_4S$: C, 53.70; H, 3.79; N, 19.28.
Found: C, 53.33; H, 3.73; N, 19.53.

EXAMPLE 28

Preparation of 2-benzylthio-5-methoxy-6-methyl-1,2,4-triazolo[1,5-a]pyrimidine

This material was prepared in 64% yield by reaction of 2-benzylthio-5-chloro-6-methyl-1,2,4-triazolo[1,5-a]pyrimidine with sodium methoxide following the general procedure described in Example 22. The desired product was isolated as a solid, m.p. 145°–146° C. IR and ¹H NMR spectra were in agreement with the assigned structure.

Analysis:

Calculated for $C_{14}H_{14}N_4OS$: C, 58.73; H, 4.89; N, 19.58.
Found: C, 58.34; H, 4.84; N, 19.67.

EXAMPLE 29

Preparation of 2-benzylthio-6-ethoxycarbonyl-7-methyl-1,2,4-triazolo[1,5-a]pyrimidine A solution of 15 g (73 mmol) of 3-amino-5-benzylthio-1,2,4-triazole and 15.0 g (80.0 mmol) of ethyl ethoxymethyleneacetoacetate in 250 ml of glacial acetic acid was heated at reflux for 60 hours. After cooling the volume of the reaction was reduced to approximately one quarter of the original volume by evaporation at reduced pressure. The resulting residue was poured into water, and the solid which separated was collected by filtration, washed with water and dried to yield 7.88 g (33%) of the desired product as a solid, m.p. 98°–99° C. IR and ¹H NMR spectra were in agreement with the assigned structure.

Analysis:

-continued

| Example No. | R¹ | R² | Physical properties |
|---|---|---|---|
| 141 | 3-methyl-5-methylisoxazol-4-yl (CH₃ at 5, isoxazole) | -CH₂-(3,4-dichlorophenyl) | NMR*: 2.52, 5.55 |
| 142 | 3-methyl-5-methylisoxazol-4-yl | -CH₂-(2-chlorophenyl) | m.p. 168°–170° C. |
| 143 | 3-methyl-5-methylisoxazol-4-yl | -CH₂-(4-chlorophenyl) | m.p. 165°–167° C. |
| 144 | 3-methyl-5-methylisoxazol-4-yl | -CH₂-CH=CH₂ | m.p. 122°–126° C. |
| 145 | 3-methyl-5-methylisoxazol-4-yl | -CH₂-C(=O)-O-C₂H₅ | m.p. 175°–176° C. |
| 146 | (CH₃)₂C=C(SCH₃)-N=C(CH₃)- | -CH₂-C₆H₅ | m.p. 156°–158° C. |
| 147 | (CH₃)₂C=C(SCH₃)-N=C(CH₃)- | -(CH₂)₂-CH₃ | m.p. 91°–96° C. |
| 148 | (CH₃)₂C=C(SCH₃)-N=C(CH₃)- | -CH₂CN | m.p. 178°–180° C. |
| 149 | (CH₃)₂C=C(SCH₃)-N=C(CH₃)- | -CH₂-(4-methylphenyl) | m.p. 158°–159° C. |
| 150 | (CH₃)₂C=C(SCH₃)-N=C(CH₃)- | -CH₂-(3,4-dichlorophenyl) | NMR*: 5.32 |
| 151 | (CH₃)₂C=C(SCH₃)-N=C(CH₃)- | -CH₂-(2-chlorophenyl) | m.p. 158° C. |
| 152 | (CH₃)₂C=C(SCH₃)-N=C(CH₃)- | -CH₂-CH=CH₂ | m.p. 111°–112° C. |

-continued

| Example No. | R¹ | R² | Physical properties |
|---|---|---|---|
| 153 | CH₃\C=N\ / \\<br>CH₃/C—S / (CH₃ on S carbon) | —CH₂—CH=CH—CH₃ | m.p. 118° C. |
| 154 | CH₃, C₂H₅ substituted thiazoline | —CH₂—C₆H₅ | m.p. 123° C. |
| 155 | CH₃, C₂H₅ substituted thiazoline | —CH₃ | m.p. 151°–5° C. |
| 156 | CH₃, CH₃ substituted thiazoline | —(CH₂)₂—CH=CH₂ | m.p. 104°–105° C. |
| 157 | CH₃, CH₃ substituted thiazoline | —CH₂—CH=C(Cl)CH₃ | NMR*: 5.48–6.00 |
| 158 | CH₃, CH₃ substituted thiazoline | —CH(CH₃)—C(O)—CH₃ | m.p. 124°–126° C. |
| 159 | CH₃, C₂H₅ substituted thiazoline | —C₂H₅ | m.p. 139°–140° C. |
| 160 | CH₃, C₂H₅ substituted thiazoline | —(CH₂)₂—CH₃ | m.p. 99°–100° C. |
| 161 | CH₃, C₂H₅ substituted thiazoline | —(CH₂)₁₁—CH₃ | m.p. 50° C. |
| 162 | CH₃, C₂H₅ substituted thiazoline | —CH₂—CN | NMR*: 2.24 5.14 |
| 163 | CH₃, C₂H₅ substituted thiazoline | —CH₂—C₆H₄—CH₃ (para) | m.p. 119° C. |
| 164 | CH₃, C₂H₅ substituted thiazoline | —CH₂—C₆H₄—Cl (ortho) | m.p. 113°–114° C. |
| 165 | 5-methyl-2-pyridyl (CH₃ substituted pyridine) | CH₃ | m.p. 112°–114° C. |

-continued
| Example No. | R¹ | R² | Physical properties |
|---|---|---|---|
| 166 | 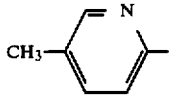 | 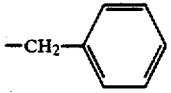 | m.p. 97°–99° C. |
| 167 | 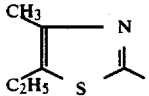 | 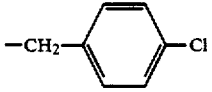 | m.p. 140°–143° C. |
| 168 | 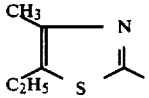 | 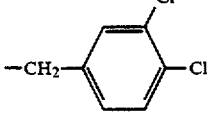 | m.p. 153°–154° C. |
| 169 | 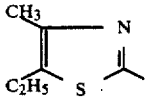 | $-CH_2-CH=CH_2$ | m.p. 83°–84° C. |
| 170 | 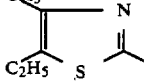 | $-CH_2-CH=CH-CH_3$ | m.p. 112°–114° C. |
| 171 | 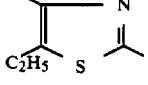 | $-(CH_2)_2-CH=CH_2$ | m.p. 102°–105° C. |
| 172 | 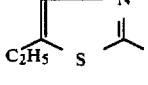 | 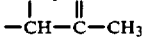 | m.p. 119°–122° C. |
| 173 | 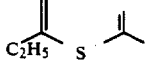 | 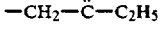 | m.p. 82°–83° C. |
| 174 | 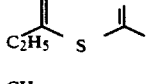 | 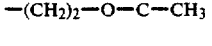 | m.p. 102°–103° C. |
| 175 | 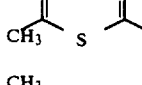 | 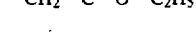 | m.p. 149°–151° C. |
| 176 | 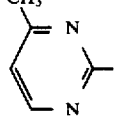 | 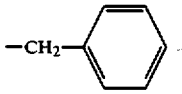 | m.p. 91°–92° C. |
| 177 | 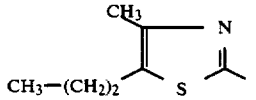 | $-CH_3$ | m.p. 123°–124° C. |
| 178 | 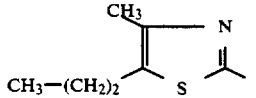 | 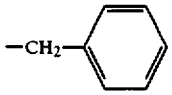 | m.p. 82°–85° C. |

-continued

| Example No. | R¹ | R² | Physical properties |
|---|---|---|---|
| 179 | CH₃–(CH₂)₂–C(=N–)–S–C(CH₃)= with CH₃ (thiazoline-type, propyl substituent) | –CH₂–CN | m.p. 122°–124° C. |
| 180 | C₆H₅–CH₂–, CH₃ on thiazoline ring | –CH₃ | m.p. 117°–118° C. |
| 181 | C₆H₅–CH₂–, CH₃ on thiazoline ring | –CH₂–C₆H₅ | m.p. 140°–141° C. |
| 182 | C₆H₅–CH₂–, CH₃ on thiazoline ring | –CH₂–CN | m.p. 162°–163° C. |
| 183 | CH₃–isoxazole | –CH₂–CH=CH–CH₃ | m.p. 143° C. |
| 184 | CH₃–isoxazole | –(CH₂)₂–CH=CH₂ | m.p. 152°–154° C. |
| 185 | CH₃–isoxazole | –CH₂–CH=C(Cl)(CH₃) | m.p. 128°–130° C. |
| 186 | CH₃–isoxazole | –(CH₂)₂–O–C(=O)–CH₃ | m.p. 140°–143° C. |
| 187 | CH₃–isoxazole | –CH₂–C≡CH | m.p. 144°–146° C. |
| 188 | CH₃–CH(OH)–(CH₂)₂– | –(CH₂)₂–CH₃ | NMR*: 1.22, 4.4 |
| 189 | CH₃–CH(OH)–(CH₂)₂– | –(CH₂)₁₁–CH₃ | NMR*: 0.9, 4.4 |
| 190 | CH₃–CH(OH)–(CH₂)₂– | –CH₂–C(=O)–O–C₂H₅ | NMR*: 1.23, 4.92 |
| 191 | CH₃–CH(OH)–(CH₂)₂– | –(CH₂)₂–O–C(=O)–CH₃ | NMR*: 1.25, 2.12 |
| 192 | CH₃–CH(OH)–(CH₂)₂– | –CH₂–CH=CH₂ | NMR*: 1.23, 4.9 |
| 193 | CH₃–CH(OH)–(CH₂)₂– | –CH₂–CH=CH–CH₃ | NMR*: 1.25, 1.8 |

-continued

| Example No. | R¹ | R² | Physical properties |
|---|---|---|---|
| 194 | CH$_3$—CH(OH)—(CH$_2$)$_2$— | —CH$_2$—CH=C(Cl)(CH$_3$) | NMR*: 1.23 2.2 |
| 195 | CH$_3$—CH(OH)—(CH$_2$)$_2$— | —CH$_2$—C≡CH | NMR*: 1.23 4.98 |
| 196 | CH$_3$—CH(OH)—(CH$_2$)$_2$— | —CH$_2$—CH$_2$—CH=CH$_2$ | NMR*: 1.23 4.48 |
| 197 | CH$_3$—CH(OH)—(CH$_2$)$_2$— | —CH$_2$—C$_6$H$_4$—Cl (4-Cl) | NMR*: 1.22 5.35 |
| 198 | CH$_3$—CH(OH)—(CH$_2$)$_2$— | —CH$_2$—C$_6$H$_4$—Cl (2-Cl) | NMR*: 1.22 5.52 |
| 199 | CH$_3$—CH(OH)—(CH$_2$)$_2$— | —CH$_2$—C$_6$H$_3$Cl$_2$ (2,3-diCl) | NMR*: 1.23 5.32 |
| 200 | CH$_3$—CH(OH)—(CH$_2$)$_2$— | —CH$_2$—C$_6$H$_5$ | NMR*: 1.23 5.41 |
| 201 | C$_6$H$_5$—CH(OH)—CH$_2$— | —CH$_3$ | m.p. 92°-93° C. |
| 202 | C$_6$H$_5$—CH(OH)—CH$_2$— | —CH$_2$—C$_6$H$_5$ | NMR*: 4.8-4.87 |
| 203 | [O—(CH$_2$)$_2$—] [HO—(CH$_2$)$_2$] CH— | —CH$_3$ | NMR*: 3.7-3.8 4.25 |
| 204 | [O—(CH$_2$)$_2$—] [HO—(CH$_2$)$_2$] CH— | —C$_2$H$_5$ | NMR*: 3.7-3.8 4.5 |
| 205 | [O—(CH$_2$)$_2$—] [HO—(CH$_2$)$_2$] CH— | —(CH$_2$)$_2$—CH$_3$ | NMR*: 3.7-3.8 4.41 |
| 206 | [O—(CH$_2$)$_2$—] [HO—(CH$_2$)$_2$] CH— | —(CH$_2$)$_2$—O—C(=O)—CH$_3$ | NMR*: 3.7-3.8 2.1 |
| 207 | [O—(CH$_2$)$_2$—] [HO—(CH$_2$)$_2$] CH— | —CH$_2$—CH=CH$_2$ | NMR*: 3.7-3.8 4.9 |
| 208 | [O—(CH$_2$)$_2$—] [HO—(CH$_2$)$_2$] CH— | —CH$_2$—CH=CH—CH$_3$ | NMR*: 1.78-3.7-3.8 |

-continued

| Example No. | R¹ | R² | Physical properties |
|---|---|---|---|
| 209 | HO—(CH₂)₂—CH(O—(CH₂)₂—) | —CH₂—C₆H₄—Cl (4-Cl) | NMR*: 3.7–3.8, 5.38 |
| 210 | HO—(CH₂)₂—CH(O—(CH₂)₂—) | —CH₂—C₆H₅ | NMR*: 3.7–3.8, 5.35 |
| 211 | HO—(CH₂)₂—CH(O—(CH₂)₂—) | —CH₂—C₆H₄—Cl (2-Cl) | NMR*: 3.7–3.8, 5.53 |
| 212 | HO—(CH₂)₂—CH(O—(CH₂)₂—) | —CH₂—C₆H₃—Cl₂ (3,4-Cl₂) | NMR*: 3.7–3.8, 5.35 |
| 213 | HO—(CH₂)₂—CH(O—(CH₂)₂—) | —CH₂—C₆H₅ | NMR*: 3.7–3.8, 5.41 |
| 214 | CH₃—CH(OH)—CH₂— | —CH(CH₃)—C(O)—CH₃ | NMR*: 1.22, 2.22 |
| 215 | 1,3-dimethylpyrazol-5-yl (N-CH₃) | —CH₃ | m.p. 116°–120° C. |
| 216 | 5-chloro-2-(benzoxazinyl)—CH₂— | —CH₃ | m.p. 129° C. |
| 217 | 2-phenylthiazol-4-yl—CH₂— | —CH₃ | NMR*: 3.95, 4.27 |
| 218 | 2-pyridyl—CH₂—CH₂— | —CH₃ | m.p. 77° C. |
| 219 | 1-methylpyrrol-2-yl—CH₂—CH₂— | —CH₃ | NMR*: 2.85, 3.6, 4.23 |
| 220 | 4,5-dimethyloxazol-2-yl | —CH₃ | m.p. 196° C. |

-continued

| Example No. | R¹ | R² | Physical properties |
|---|---|---|---|
| 221 | HO—(CH₂)₃— | —CH₃ | NMR*: 3.75 4.28 |
| 222 | HO—(CH₂)₂—O(CH₂)₂— | —CH₂—C(=O)—OC₂H₅ | NMR*: 4.9 |
| 223 | HO—(CH₂)₂—O(CH₂)₂— | —CH₂—C(CH₃)(=O)—CH₃ | NMR*: 2.21 |
| 224 | HO—(CH₂)₅— | CH₃ | NMR*: 4.23 |
| 225 | HO—(CH₂)₅— | C₂H₅ | NMR*: 4.49 |
| 226 | HO—(CH₂)₅— | —(CH₂)₂—CH₃ | NMR*: 4.38 |
| 227 | HO—(CH₂)₅— | —CH₂—CN | NMR*: 5.11 |
| 228 | HO—(CH₂)₅— | —CH₂—CH₂—O—C(=O)—CH₃ | NMR*: 2.1 |
| 229 | HO—(CH₂)₅— | —CH₂—CH=CH₂ | NMR*: 4.9 |
| 230 | HO—(CH₂)₅— | —CH₂—CH=CH—CH₃ | NMR*: 4.8 |
| 231 | HO—(CH₂)₅— | —CH₂—(4-Cl-C₆H₄) | NMR*: 5.38 |
| 232 | HO—(CH₂)₅— | —CH₂—(2,3-Cl₂-C₆H₃) | NMR*: 5.35 |
| 233 | HO—(CH₂)₅— | —CH₂—C₆H₅ | NMR*: 5.4 |
| 234 | 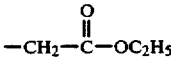 | —CH₂CN | m.p. 199° C. |
| 235 | 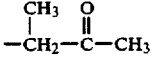 | —CH₂—CO—CH₃ | m.p. 169° C. |
| 236 | 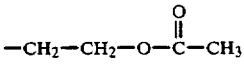 | 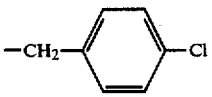 | m.p. 180° C. |
| 237 | 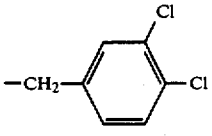 | 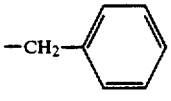 | m.p. 166° C. |
| 238 | 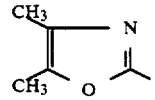 | 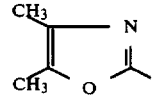 | m.p. 190° C. |
| 239 | 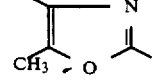 | —CH₂—CN | ¹H—NMR*: 5.2 |

-continued

| Example No. | R¹ | R² | Physical properties |
|---|---|---|---|
| 240 | CH₃-C(=N-O-C(CH₃))-CH₃ (isoxazole) | -CH₂-C(=N-O)-C(CH₃)₃ (isoxazoline) | m.p. 95° C. |
| 241 | CH₃-C(=N-O-C(CH₃))-CH₃ | -CH₂-CO-OC₂H₅ | m.p. 158° C. |
| 242 | CH₃-C(=N-O-C(CH₃))-CH₃ | -CH₂-C(=N-S)-CH₃ | NMR*: 5.5 |
| 243 | pyridin-2-yl-CH(CH₃)- | -CH₂CN | NMR*: 8.25 |
| 244 | pyridin-2-yl-CH(CH₃)- | -CH₂-CO-OC₂H₅ | m.p. 131° C. |
| 245 | pyridin-3-yl-CH(CH₃)- | -CH₂-CO-OC₂-H₅ | m.p. 137° C. |
| 246 | pyridin-3-yl-CH(CH₃)- | -CH₂-CO-CH₃ | ¹H—NMR*: 5.3 |
| 247 | pyridin-4-yl-CH(CH₃)- | -CH₂-CO-OC₂H₅ | NMR*: 6.8 |
| 248 | C₂H₅-CH(OH)-CH₂- | CH₃ | ¹H—NMR*: 0.98; 4.25 |
| 249 | (C₂H₅)₂CH-CH(OH)-CH₂- | CH₃ | ¹H—NMR*: 0.92;- 4.22 |

*The ¹H NMR spectra were recorded in CDCl₃ or in DMSO—d₆. The chemical shift is given as the value in ppm.

Preparation of the starting compounds

EXAMPLE II-1

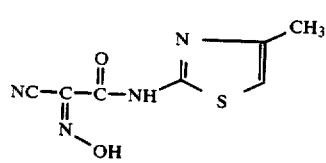

5.4 g (0.03 mol) of 2-cyanoacetamido-4-methyl-thiazole are dissolved in 30 ml of ethanol, and 3.9 g (0.033 mol) of isoamyl nitrite are added. 16.5 ml of 2N HCl are then added, and the mixture is allowed to stand at room temperature for 1 hour. After cooling to 0° C., the product is filtered off.

4.9 g (77% of theory) of N-(4-methylthiazol-2-yl)-2-hydroximinocyanoacetamide of decomposition point 252° C. are obtained.

The following 2-cyano-2-oximinoacetamides of the general formula (II) are obtained in the corresponding fashion and according to the general instructions for the preparation:

$$\underset{\underset{OM}{\overset{\|}{N}}}{NC-C-\overset{\overset{O}{\|}}{C}-NH-R^1} \quad (II)$$

| Example No. | R¹ | M | Physical properties |
|---|---|---|---|
| II-2 | 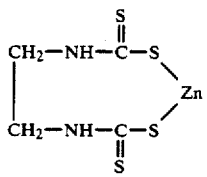 | H | Decomposition point 238° C. |
| II-3 | 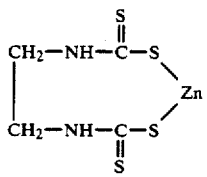 | H | m.p. 178–180° C. |

Use examples:

In the following use examples, the compound shown below was employed as comparison substance:

$$\begin{array}{c} CH_2-NH-\overset{\overset{S}{\|}}{C}-S \\ | \qquad\qquad\qquad\quad \diagdown \\ \qquad\qquad\qquad\qquad\quad Zn \\ | \qquad\qquad\qquad\quad \diagup \\ CH_2-NH-\underset{\underset{S}{\|}}{C}-S \end{array}$$

Zinc ethylene-1,2-bis-dithiocarbamate

EXAMPLE A

Phytophthora test (tomato)/curative
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are inoculated with an aqueous spore suspension of Phytophthora infestans. The plants remain in an incubation cabin at 20° C. and 100% relative atmospheric humidity for 7 hours. After a short drying off time, the plants are sprayed with the preparation of active compound until dripping wet.

The plants are placed in an incubation cabin at 100% relative atmospheric humidity and at about 20° C.

Evaluation is carried out 3 days after the inoculation.

In this test, a clearly superior activity compared with the prior art is shown, for example, by the compounds according to the following Preparation Examples: 2, 4, 5, 6, 7, 11, 12, 13, 27, 28, 29, 30, 32, 33, 34, and 120.

It will be understood that the specification and examples are illustrative but not limitative of the present invention and that other embodiments within the spirit and scope of the invention will suggest themselves to those skilled in the art.

We claim:

1. A 2-cyano-2-alkoximino-acetamide of the formula $$\underset{\underset{O-R^2}{\overset{\|}{N}}}{NC-C-\overset{\overset{O}{\|}}{C}-NH-R^1}$$

in which
  $R^1$ represents in each case straight-chain or branched, optionally phenyl-substituted hydroxyalkyl or hydroxyalkoxyalkyl in each case having 1 to 6 carbon atoms in the individual alkyl parts,
  $R^2$ represents straight-chain or branched alkyl, having 1 to 18 carbon atoms, which is optionally monosubstituted or polysubstituted, the substituents being identical or different and being cyano, in each case straight-chain or branched alkanoyl, alkoxycarbonyl or alkylcarbonyloxy in each case having 1 to 6 carbon atoms in the individual alkyl parts, and phenyl or heteroaryl which is in each case optionally monosubstituted or polysubstituted by lower alkyl and/or halogen; and in addition represents in each case straight-chain or branched alkenyl or halogenoalkyl in each case having 3 to 8 carbon atoms and, in the case of halogenoalkenyl, having 1 to 5 halogen atoms, or straight-chain or branched alkinyl having 3 to 8 carbon atoms, the heteroaryl when present being pyridyl, pyrimidyl, triazinyl, quinolyl, isoquinolyl, oxazolyl, isoxazolyl, oxadiazolyl, benzoxazolyl, thiazolyl, isothiazolyl, thiadiazolyl, benzthiazolyl, imidazolyl, benzimidazolyl, pyrrolyl, furanyl, thienyl, pyrazolyl or triazolyl.

2. A 2-cyano-2-alkoximino-acetamide according to claim 1, in which
  $R^1$ represents in each case straight-chain or branched, optionally phenyl-substituted hydroxyalkyl or hydroxyalkoxyalkyl in each case having 1 to 4 carbon atoms in the individual alkyl parts, in addition represents heteroarylalkyl or heteroaryl, in each case having 2 to 10 carbon atoms and 1 to 3 nitrogen and/or oxygen and/or sulphur atoms in the heteroaryl part and 1 to 4 carbon atoms in the straight-chain or branched alkyl part, which is in each case optionally monosubstituted, disubstituted or trisubstituted and/or benzene-fused, the substituents being identical or different and substituents in the heteroaryl part and/or in the benzene-fused ring being hydroxyl, fluorine, chlorine, bromine, cyano, methyl, ethyl, n- or i- propyl, n-, i-, s- or t-butyl, allyl, butenyl, methoxy, ethoxy, methylthio, benzyl, phenyl, acetyl, propionyl, methoxycarbonyl, ethoxycarbonyl, methylaminocarbonyl or dimethylaminocarbonyl, and
  $R^2$ represents straight-chain or branched alkyl, having 1 to 12 carbon atoms, which is optionally monosubstituted, disubstituted or trisubstituted, the substituents being identical or different and being cyano, acetyl, propionyl, methoxycarbonyl, ethoxycarbonyl, methylcarbonyloxy, ethylcarbonyloxy, or phenyl or heteroaryl which is optionally monosubstituted, disubstituted or trisubstituted by fluorine, chlorine, bromine, methyl and/or ethyl, the substituents being identical or different, or in addition represents in each case straight-chain or branched alkenyl or halogenalkenyl having 3 to 6 carbon atoms and, if appropriate 1 to 3 halogen atoms, or straight-chain or branched alkinyl having 3 to 6 carbon atoms.

3. A 2-cyano-2-alkoximino-acetamide according to claim 1, in which

R¹ represents in each case straight-chain or branched, optionally phenyl-substituted hydroxyalkyl or hydroxyalkoxyalkyl in each case having 1 to 4 carbon atoms in the individual alkyl parts, or, additionally, represents heteroaryl or heteroarylalkyl, having 1 to 4 carbon atoms in the straight-chain or branched alkyl part, which is in each case optionally monosubstituted, disubstituted or trisubstituted, the substituents being identical or different, the heteroaryl radical being pyridyl, pyrimidyl, triazinyl, quinolyl, isoquinolyl, oxazolyl, isoxazolyl, oxadiazolyl, benzoxazolyl, thiazolyl, isothiazolyl, thiadiazolyl, benzthiazolyl, imidazolyl, benzimidazolyl, pyrrolyl, furanyl, thienyl, pyrazolyl or triazolyl, and the substituents in the heteroaryl part or in the benzene-fused ring being hydroxyl, fluorine, chlorine, bromine, cyano, methyl, ethyl, n- or i-propyl, n-, i-, s- or t-butyl, allyl, butenyl, methoxy, ethoxy, methylthio, benzyl, phenyl, acetyl, propionyl, methoxycarbonyl, ethoxycarbonyl, methylaminocarbonyl or dimethylaminocarbonyl, and R² represents straight-chain or branched alkyl, having 1 to 12 carbon atoms, which is optionally monosubstituted, disubstituted or trisubstituted, the substituents being identical or different and being cyano, acetyl, propionyl, methoxycarbonyl, ethoxycarbonyl, methylcarbonyloxy, ethylcarbonyloxy, or phenyl which is optionally monosubstituted, disubstituted or trisubstituted by fluorine, chlorine, bromine, methyl and/or ethyl, the substituents being identical or different; in addition represents in each case straight-chain or branched alkenyl or halogenoalkenyl having 3 to 6 carbon atoms and, if appropriate, 1 to 3 halogen atoms, or straight-chain or branched alkinyl having 3 to 6 carbon atoms.

4. A compound according to claim 1, wherein such compound is 1-(2-cyano-2-ethoximino-acetamido)-ethanol of the formula

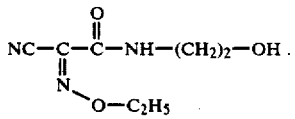

5. A compound according to claim 1, wherein such compound is 1-(2-cyano-2-methoximino-acetamido)-2-hydroxy-propane of the formula

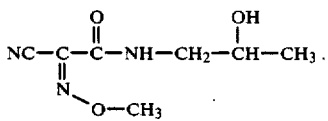

6. A fungicidal composition comprising a fungicidally effective amount of a compound according to claim 1, and a diluent.

7. A method of combating fungi which comprises applying to such fungi or to a fungus habitat a fungicidally effective amount of a compound according to claim 1.

8. The method according to claim 7, wherein such compound is
2-(2-cyano-2-methoximino-acetamido)-4-methyl-thiazole,
2-(2-cyano-2-benzyloximino-acetamido)-4-methyl-thiazole,
2-(2-cyano-2-methoximino-acetamido)-4,5-dimethyl-thiazole,
1-(2-cyano-2-ethoximino-acetamido)-ethanol or
1-(2-cyano-2-methoximino-acetamido)-2-hydroxy-propane.

9. A 2-cyano-2-oximino-acetamide of the formula

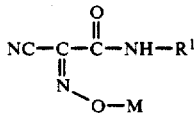

in which
M represents hydrogen or an alkali metal cation, and
R¹ represents in each case straight-chain or branched optionally phenyl-substituted hydroxyalkyl or hydroxyalkoxyalkyl in each case having 1 to 6 carbon atoms in the individual alkyl parts.

* * * * *

UNITED STATES PATENT AND TRADEMARK OFFICE
CERTIFICATE OF CORRECTION

PATENT NO. : 4,886,833

DATED : December 12, 1989

INVENTOR(S) : Gayer et al.

It is certified that error appears in the above-identified patent and that said Letters Patent is hereby corrected as shown below:

Title Page  FOREIGN PATENT DOCUMENTS: After " 0206004, 12/1986, European Pat. Off."add -- 558/445 --;

Title Page  ABSTRACT: 2nd line from bottom delete " Intermediate " and substitute -- Intermediates --.

Col. 50, line 12, claim 1, after " parts, " add -- and --.

Signed and Sealed this

Twenty-fourth Day of December, 1991

Attest:

HARRY F. MANBECK, JR.

Attesting Officer

Commissioner of Patents and Trademarks